United States Patent [19]

Tanaka et al.

[11] 4,139,692

[45] Feb. 13, 1979

[54] COPOLYMER FOR CONTACT LENS, ITS PREPARATION AND CONTACT LENS MADE THEREOF

[75] Inventors: Kyoichi Tanaka; Kouzou Takahashi, both of Nagoya; Mitsuhiro Kanada, Aichi; Yasuyuki Kato, Kasugai; Masuji Ichihara, Aichi, all of Japan

[73] Assignee: Toyo Contact Lens Co., Ltd., Nagoya, Japan

[21] Appl. No.: 888,314

[22] Filed: Mar. 20, 1978

[30] Foreign Application Priority Data

Oct. 12, 1977 [JP] Japan .................................. 52-122680

[51] Int. Cl.$^2$ ................... C08F 220/28; C08F 230/08; G02C 7/04
[52] U.S. Cl. ............................... 526/218; 204/159.22; 260/29.6 TA; 351/160 R; 526/232; 526/264; 526/279
[58] Field of Search ............... 526/264, 279, 218, 232; 204/159.22; 351/160; 260/29.6 TA

[56] References Cited

U.S. PATENT DOCUMENTS

| | | | |
|---|---|---|---|
| 3,787,380 | 1/1974 | Stamberger | 526/264 |
| 3,937,680 | 2/1976 | de Carle | 526/264 |
| 3,951,893 | 4/1976 | Gander | 526/279 |
| 4,022,754 | 5/1977 | Howes et al. | 526/264 |

FOREIGN PATENT DOCUMENTS

5233502   8/1977   Japan.

*Primary Examiner*—Harry Wong, Jr.
*Attorney, Agent, or Firm*—Armstrong, Nikaido, Marmelstein & Kubovcik

[57] ABSTRACT

A copolymer suitable for use as contact lenses, comprising a polymerization product of (a) at least one monomer selected from methyldi(trimethylsiloxy)sylylpropylglycerol methacrylate and methyldi(trimethylsiloxy)sylylpropylglycerolethyl methacrylate, (b) a hydrophilic monomer, (c) a methacrylic acid alkyl ester and (d) a cross-linking agent having at least two copolymerizable functional groups. Contact lenses made of the above copolymer has excellent oxygen permeability and can be comfortably worn continuously for a long term without a foreign body sensation and pain.

11 Claims, No Drawings

COPOLYMER FOR CONTACT LENS, ITS PREPARATION AND CONTACT LENS MADE THEREOF

BACKGROUND OF THE INVENTION

The present invention relates to a novel copolymer and the preparation thereof, and more particularly to a copolymer suitable for use in contact lenses.

The present invention also relates to contact lenses which can be worn continuously for a long term without pain, and more particularly to contact lenses made of a novel copolymer having an excellent oxygen permeability which is increased by introducing a siloxane at branching chain ends of a polymer chain.

Contact lenses are generally classified into two large groups of the hard type and the soft type.

The hard type contact lenses are made of polymethyl methacrylate. Such contact lenses have a history of several tens of years, but are still insufficient for use in visual correction. The contact lenses made of polymethyl methacrylate give a foreign body sensation to many persons and the use of the contact lenses is often given up in the early stage of wear. Also, even persons who can bear the foreign body sensation take about one month for accommodation before they can wear the contact lenses for over 12 hours, and for this trouble, some of them give up the use of the contact lenses. Further, even persons who have accommodated to the use of the contact lenses and have been in no pain, always have a feeling of wearing contact lenses on eyes. Also, when the wear of the contact lenses is stopped for several days, the period of accommodation is required again. That is to say, for wearing the contact lenses made of polymethyl methacrylate all day there are required a period of bearing a foreign body sensation and a period of accommodating to the foreign body. This is due to the fact that since the use of the contact lenses made of polymethyl methacrylate is a burden on a respiration of the cornea (which takes oxygen from air because of the nonvessel tissue) because of its low oxygen permeability, it is required to minimize interception between cornea and air by the contact lenses and, therefore, the size of the contact lenses must be made as small as possible and also the contact lenses must be worn to move on cornea by making the curve of the inner surface of the lens larger than the radius of curvature of cornea so that tears containing oxygen might readily circulate between cornea and the lens, by which users have a stronger foreign body sensation.

Also, there exist persons who cannot wear the contact lenses all day and only wear for 5 to 6 hours a day, since when wearing for a long time, ocular congestion occurs, vision becomes blur or they feel a weariness. This is caused by the fact that in case of such persons, since the amount of tears is small, the supply of oxygen is small and, therefore, cornea lacks in oxygen and transforms.

Accordingly, there has been desired contact lenses which does not give a foreign body sensation and can be comfortably worn without pain. Soft type contact lenses were developed to satisfy such demands. However, so developed soft contact lenses are also not satisfactory for the following reasons.

Two kinds of soft contact lenses are known. One is those prepared from poly-2-hydroxyethyl methacrylate, and the other is those prepared from a hydrophobic silicone rubber.

Since the silicone rubber lenses are very water-repellent and are greatly different from cornea in thermal properties such as thermal conductivity and thermal diffusivity, they give a foreign body sensation, particularly a burning sensation, despite that the oxygen permeability is very large and, therefore, there is required a stronger patience than the case of polymethyl methacrylate lenses to accommodate to the silicone rubber lenses. Further, the silicone rubber is soft and elastic, and precise mechanical treatments thereof such as cutting, grinding and polishing are very difficult. Also, many attempts to make the surface of silicone rubber lenses hydrophilic have been reported, but a satisfactory silicone rubber contact lens has never been developed.

The contact lenses made of poly-2-hydroxyethyl methacrylate absorb water and become flexible and, therefore, the stability of visual power is designed by making the size of lens large. Accordingly, a feeling in wear is very good. However, since the water content of the lens is at most 40 % by weight, the permeation of oxygen through water as a medium is small and it is impossible to continuously wear the lenses for a long period of time. According to Journal of Japan Contact Lens Society, Vol, 12, No. 10, 142 (1970), it is reported that oxygen required for the cornea in respiration is about 12 to 20 mmHg. in partial pressure of oxygen on cornea during wear of contact lenses. In case of the contact lenses made of poly-2-hydroxyethyl methacrylate having a thickness of about 0.2 mm., the oxygen partial pressure is only about 5.5 to 6 mmHg. Therefore, the problem of corneal respiration cannot be completely solved also by such contact lenses. For such a reason, the contact lenses made of poly-2-hydroxyethyl methacrylate are worn flat so as to move with every winking, by which tears can circulate between cornea and lens. Therefore, the lens are gradually soiled during wear or by awkward handling and when the movement of the lens on cornea becomes small, exchange of tears decreases and in conjunction with the lens being large in size, corneal troubles become easy to occur.

As stated above, it is an essential condition for enabling the continuous, safety wear of contact lenses for a long term that the oxygen permeability is large, and it is desirable for comfortably wearing contact lenses that a foreign body sensation is as small as possible.

From such a point of view, high water content contact lenses having excellent oxygen permeability which are made of a polyvinyl pyrrolidone as a main component have been proposed and reported, but these contact lenses are also unsatisfactory for continuous wear. For instance, polyvinyl pyrrolidone lens of a certain kind is extremely colored or is translucent. Also, a certain lens is so weak in quality of material that a user himself cannot handle it freely. In general, a material of high water content has the defects that the stability in shape of lens is bad as a result of containing water in large quantities and, therefore, the dimensions of lens may easily be changed even by changes in temperature of tears, pH and osmotic pressure, and that a lens contour transforms during the use of a long term and the refractive power, size and base-curve of the lens changes, by which the life of the contact lens is shortened. Further, there is a serious problem in the lens of this type that the lens with high water content is contaminated by bacteria. For solving this problem, boiling treatment, chemical sterilization treatment, etc. are considered, but these are troublesome. Moreover, the boiling treatment accelerates the deterioration in quality of material and the chemical sterilization treatment incurs danger to eyes.

Further, the high water content contact lens has the fatal disadvantage that the optical properties change at the time of wearing. That is to say, the water content of the contact lens undergoes a change with external environment, and this brings about changes in refractive index, size, base-curve, front-curve and transparency of the lens, by which the visual correction ability is lowered. Such a change in water content of the lens is mainly caused by the evaporation of water from the surface, particularly the outer surface of the lens. The higher the water content and the thinner the lens, the larger the change in optical properties. At times, the evaporation rate of water is too large and the water supply to a lens by tears is late, and as a result, the edge of the lens is warped and sometimes the lenses fall from eyes.

As stated above, conventional contact lenses are not necessarily suitable for continuous wear for a long term.

OBJECTS OF THE INVENTION

It is an object of the present invention to provide a novel copolymer suitable for use in contact lenses.

A further object of the present invention is to provide a contact lens which can be continuously worn for a long term.

A still further object of the invention is to provide a contact lens which can be worn comfortably without giving a foreign body sensation and pain.

Another object of the invention is to provide a contact lens having an excellent oxygen permeability and a proper hydrophilic property.

These and other objects of the invention will become apparent from the description hereinafter.

DETAILED DESCRIPTION

It has now been found that the above-mentioned objects can be attained by polymerization products consisting essentially of (a) 30 to 80 % by weight of at least one monomer selected from the group consisting of methyldi(trimethylsiloxy)sylylpropylglycerol methacrylate having the following formula [I]

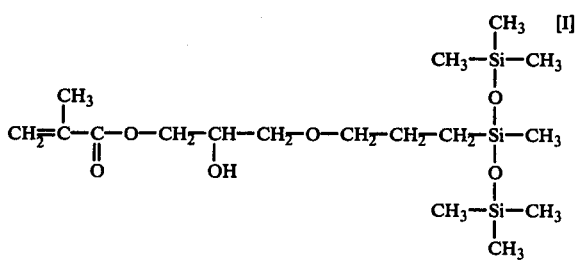

and methyldi(trimethylsiloxy)sylylpropylglycerolethyl methacrylate having the following formula [II]

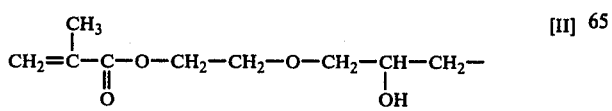

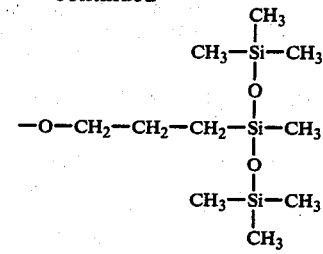

(b) 5 to 30% by weight of a hydrophilic monomer, (c) 5 to 60% by weight of a methacrylic acid alkyl ester monomer, and (d) 0.5 to 15% by weight of a cross-linking agent having at least two copolymerizable functional groups.

To eliminate the defects of conventional contact lenses, it is required (1) that the oxygen permeability of a contact lens is large enough to be able to continuously wear the lens for a long term, (2) that the lens does not absorb water, but has the hydrophilic property to the extent that the lens gets to fit the eye, and (3) that a user can wear without feeling a foreign body sensation. The contact lens made of the above novel copolymer of the present invention satisfies all of the above requirements. According to the present invention, the oxygen permeability is increased by introducing a siloxane at branching chain ends of a polymer chain, and the problem of the strong water-repellent property brought about by the introduction of the siloxane bonds is solved by copolymerizing with the hydrophilic monomer so that the lens does not absorb water, but has sufficient hydrophilic property to get to fit eye. Also, the foreign body sensation can be eliminated by making the lens size large on the basis of the increase of the oxygen permeability. The novel hard type contact lens of the present invention can be comfortably worn continuously for a long term.

As stated before with respect to the silicone rubber lenses, it is well known, for instance, in Japanese Patent Disclosure No. 87184/1975 that the utilization of a siloxane bond is an available means for increasing the oxygen permeability.

In contrast to such a known art, the feature of the present invention lies in the use of the particular methacrylic acid ester derivative which contains not only the siloxane bond, but also hydroxyl group and ether bond which are hydrophilic. The methacrylic acid ester derivative employed in the present invention is methyldi(-trimethylsiloxy)sylylpropylglycerol methacrylate of the formula [I] (hereinafter referred to as "SiGMA") and methyldi(trimethylsiloxy)sylylpropylglycerolethyl methacrylate of the formula [II] (hereinafter referred to as "SiGEMA"), which are novel compounds. The methacrylic acid ester derivatives may be employed singly or in admixture thereof.

As seen in the structural formulas [I] and [II], SiGMA and SiGEMA contain a hydroxyl group and ether bond in the molecule. This is very important for making long-term, continuous wear of contact lenses possible.

In general, polymers prepared from a monomer containing a siloxane bond, particularly a monomer containing a siloxane bond but containing no hydrophilic group have a strong water-repellent property and therefore, such polymers cannot be employed as a material of contact lens, unless the monomer is copolymerized with a hydrophilic monomer. However, when copolymerizing a hydrophobic monomer with a hydrophilic monomer, the products are liable to become opaque. This is a fatal defect in use as a material of contact lens. Therefore, the proportion of a hydrophobic monomer having no hydrophilic group to a hydrophilic monomer is limited for producing transparent copolymer, and thus desirable contact lenses cannot be obtained. That is to say, for obtaining the oxygen permeability enough to make the continuous wear possible, it is necessary to increase the number of the siloxane bond. However, the more the number of the siloxane bond increases, the stronger the undesirable water-repellent property becomes, and for this reason, a larger amount of a hydrophilic monomer must be copolymerized. However, in case of a hydrophobic monomer having no hydrophilic group, it is hard to copolymerize with a hydrophilic monomer, and consequently, when a large amount of the hydrophilic monomer is employed, the produced copolymer becomes opaque. On the other hand, in order to produce a transparent copolymer, the number of the siloxane bond must be decreased, and a copolymer having a sufficient oxygen permeability cannot be obtained.

In contrast, SiGMA and SiGEMA employed in the present invention have a hydroxyl group and ether bond in the molecule and, therefore, are miscible with a hydrophilic monomer in all proportions and also easily copolymerizable therewith. The copolymer obtained by using SiGMA and/or SiGEMA are colorless and transparent, and are hydrophilic, and have high oxygen permeability.

For obtaining the copolymer having the oxygen permeability required in long-term, continuous wear of the contact lens, it is necessary to employ 30 to 80% by weight, preferably 45 to 65% by weight of SiGMA and/or SiGEMA based on the total weight of the monomers employed. When the amount of SiGMA and/or SiGEMA is less than the above range, the oxygen permeability is low, and when the amount is larger than the above range, the water-repellent property and flexibility are increased.

In the present invention, the hydrophilic monomer is employed to provide the contact lens with the hydrophilic property. Examples of the hydrophilic monomer employed in the present invention are ethylene glycol monomethacrylate, diethylene glycol monomethacrylate, triethylene glycol monomethacrylate, N-vinyl pyrrolidone and dimethyl acrylamide. These monomers may be employed singly or in admixture thereof. The amount of the hydrophilic monomer is from 5 to 30% by weight based on the total weight of the monomer employed. When the amount of the hydrophilic monomer is less than 5% by weight, the water-repelling becomes strong. Also when the amount is more than 30% by weight, the obtained copolymer is water-retainable. Thus, the copolymer is plasticized by containing water and becomes flexible.

A copolymer consisting of only two kinds of the above-mentioned monomers, i.e. the above-mentioned monomers (a) and (b), has the drawback in processing. That is to say, such a copolymer is too flexible and, therefore, is hard particularly to polish upon preparing contact lenses from the copolymer and moreover the finished lens is poor in properties as a hard lens. In the present invention, in order to eliminate this drawback, the cross-linkable monomer having at least two copolymerizable functional groups (which is hereinafter referred to as "cross-linking agent") is copolymerized with the above-mentioned monomers. Examples of the cross-linking agent employed in the present invention are ethylene glycol dimethacrylate, diethylene glycol dimethacrylate, triethylene glycol dimethacrylate, allyl methacrylate, divinyl benzene, diallyl phthalate and trimethylolpropane trimethacrylate. These cross-linking agents may be employed singly or in admixture thereof. The amount of the cross-linking agent is from 0.5 to 15% by weight based on the total weight of the monomers employed. The copolymer having good processing property is obtained within the above range. When the amount is less than the above range, the obtained copolymer is flexible and is hard to polish, and when the amount is more than the above range, the obtained copolymer is hard and fragile.

For the purpose of providing the copolymer with good cutting property and stiffness, a methacrylic acid alkyl ester monomer is employed in the present invention. The methacrylic acid alkyl ester monomer of which homopolymer has a glass transition temperature of more than room temperature, is preferred. Examples of such a methacrylic acid alkyl ester monomer are methyl methacrylate, ethyl methacrylate and cyclohexyl methacrylate. These monomers may be employed singly or in admixture. The amount of the methacrylic acid alkyl ester is from 5 to 60% by weight based on the total weight of the monomers employed.

The polymerization of the above-mentioned monomers is carried out by employing free radical polymerization initiators which are conventionally employed in the polymerization of unsaturated hydrocarbons, such as benzoyl peroxide, azobisisobutyronitrile and azobisdimethylvaleronitrile. The initiator is usually employed in an amount of 0.05 to 1.0 part by weight to 100 parts by weight of the monomer mixture.

In the present invention, any polymerization systems are applicable, and the bulk polymerization is particularly preferred by the reason that the obtained copolymer can be directly employed as a material of contact lens as it is.

The polymerization is carried out in a conventional manner. For instance, in case of the polymerization using ultraviolet ray, the monomers are first polymerized under the ultraviolet irradiation at a temperature of 15° to 50° C. for about 30 to about 40 hours, and then thermally polymerized without the ultraviolet irradiation at a temperature of 50° to 120° C. for about 30 to about 40 hours. In that case, the polymerization may be carried out by stepwise raising the temperature. For instance, the monomers are polymerized first at 15° C. for about 16 hours, and at 40° C. for about 8 hours and finally at 50° C. for about 8 hours under the ultraviolet irradiation, and then thermally polymerized without the ultraviolet irradiation at 60° C. for about 24 hours, and at 80° C. for about 4 hours, and at 100° C. for about 4 hours and further at 120° C. for about 4 hours. When carrying out the polymerization by only thermal polymerization technique, the polymerization is usually carried out at a temperature of 40° to 120° C. for about 60 to about 110 hours, and may be, of course, carried out stepwise. For instance, the polymerization is carried out first at 40° C. for about 64 hours, and at 60° C. for about 24 hours, and at 100° C. for about 4 hours and at 80° C. for about 4 hours, and finally at 120° C. for about 4 hours. The polymerization of the monomers has been explained above with reference to some instances, but it is to be understood that the polymerization conditions are not limited to such temperature and time conditions and the use of ultraviolet ray.

The cast polymerization is suitable for preparing contact lenses. The polymerization may be conducted in a mold having a shape of contact lens by the bulk polymerization technique, and the resulting lens having nearly desired shape is finished to a contact lens by a usual mechanical processing. Also, the monomer mixture may be thermally polymerized in an appropriate mold or vessel to give a block, sheet or rod, and it may be then mechanically treated in a conventional manner to give a contact lens of a desired shape.

The thus prepared copolymer is novel and has approximately the same composition as that of the monomer mixture employed. That is to say, the copolymer consists essentially of (a) 30 to 80 % by weight of SiGMA and/or SiGEMA units, (b) 5 to 30 % by weight of the hydrophilic monomer units, (c) 5 to 60 % by weight of a methacrylic acid alkyl ester monomer units, and (d) 0.5 to 15% by weight of a cross-linking agent units.

The copolymer of the present invention has the improved oxygen permeability as compared with a conventional polymethyl methacrylate lens material. For instance, the copolymer prepared by polymerizing 55 parts by weight of SiGMA, 10 parts by weight of ethylene glycol monomethacrylate, 5 parts by weight of ethylene glycol dimethacrylate and 30 parts by weight of methyl methacrylate has the oxygen permeability of about $14.9 \times 10^{-10}$ ml.cm./cm$^2$.sec.cmHg. On the other hand, the oxygen permeability of a lens made of polymethyl methacrylate is about $0.05 \times 10^{-10}$ ml.cm./cm$^2$.sec.cmHg, and also the oxygen permeability of a lens made of poly-2-hydroxyethyl methacrylate which contains water in saturation is about $5.6 \times 10^{-10}$ ml.cm./cm$^2$.sec.cmHg.

The oxygen permeability of the above copolymer of the invention prepared by employing 55 parts by weight of SiGMA is about 300 times that of a conventional polymethyl methacrylate lens and is about 2.7 times that of a conventional poly-2-hydroxyethyl methacrylate soft lens containing water. This fact means that the copolymer of the present invention has the oxygen permeability necessary for enabling the contact lens made thereof to be worn continuously for a long term, because it is reported that a poly-2-hydroxyethyl methacrylate contact lens having a thickness of 0.2 mm, can permeate oxygen of about ½ time the required oxygen. In fact, according to the present inventor's clinical study in which contact lenses having a thickness of 0.15 mm., a size of 11.5 mm. and a radius of curvature of inner surface of 7.90 mm. were prepared from the novel copolymer of the present invention and were continuously worn on albino rabbit eyes for 21 days, no change was observed on corneal surfaces and there was no decrease of glycogen, and also in respect of the histological observation, there was no vascularization, substantial edema and infiltration of inflammatory cells and like this, no morpholotically significant change was observed. The reason that the continuous wear was conducted for 21 days is that it is known that the cycle of metabolism of cornea is about 18 days.

The oxygen permeability of the copolymer of the present invention is in proportion to the content of SiGMA or SiGEMA, and the copolymer containing 30 to 80 % by weight of SiGMA and/or SiGEMA has an oxygen permeability of about $3.0 \times 10^{-10}$ to about $31.1 \times 10^{-10}$ ml.cm./cm$^2$.sec.cmHg. The refractive index of the copolymer of the invention varies depending on the kind and amount of the employed monomers, but falls within the range of $n_D^{20} = 1.40$ to 1.49. Also, the copolymer of the present invention has a specific gravity of from 1.08 to 1.21, a visible ray percent transmission of not less than 90% and a Vickers hardness number of 4.0 to 19.0.

The copolymer of the present invention is very useful as the material of contact lens. The contact lenses of the present invention is prepared generally by subjecting moldings prepared directly by cast polymerization as stated before to a known mechanical processing.

In the instant specification, the values of the oxygen permeability, refractive index and visible ray percent transmission are those measured as follows:

The oxygen permeability is measured by an oxygen gas permeameter made by Rikaseiki Kogyo Co., Ltd, by employing specimens having a diameter of 15 mm. and a thickness of 0.1 mm.

The refractive index is measured by Abbé's refractometer made by Erma Optical Works Co., Ltd.

The visible ray percent transmission is measured by Double-Beam Spectro Photometer UV-210 made by Shimadzu Seisakusho Ltd. by employing film specimens having a thickness of 0.15 mm.

The present invention is more particularly described and explained by means of the following Example, in which all parts are parts by weight unless otherwise stated. In order to illustrate the preparation of SiGMA and SiGEMA, the following Reference Examples are also presented.

Reference Example 1

Synthesis of SiGMA
[methyldi(trimethylsiloxy)sylylpropylglycerol Methacrylate]

A one liter four neck round bottom flask equipped with a magnetic stirrer, a thermometer, a tube for introducing nitrogen gas, a dropping funnel and a reflux condenser was charged with 336 g. of methyldi(trimethylsiloxy)sylylpropyloxypropylene oxide, 6.5 g. of potassium hydroxide and 0.8 g. of hydroquinone, and was placed on an oil bath. With introducing nitrogen gas into the flask, 172 g. of methacrylic acid was added dropwise to the flask through the dropping funnel with stirring. The mixture was then gradually heated to 100° C, and at this temperature the reaction was carried out for about 7 hours. After the completion of the reaction, the reaction mixture was allowed to cool and filter to remove potassium methacrylate. The filtrate was then admixed with n-hexane and the mixture was washed several times with a 0.5N aqueous solution of sodium hydroxide by employing a separatory funnel until the aqueous solution became colorless. The mixture was further washed with a saline water until it was neutral and was then dehydrated by employing Glauber's salt for a day and night. After the dehydration, the mixture was filtered and then n-hexane was removed by an evaporator. The thus purified reaction product was a slightly viscous, transparent liquid.

According to the quantitative analysis by gas chromatography, the purity of the obtained product was over 98%.

Also, the refractive index $n_D^{20}$ of the product was 1.4546.

The infrared absorption spectrum of the product indicated absorptions of —OH group at 3,420 cm$^{-1}$, of double bond at 1,640 cm$^{-1}$, of ester bond at 1,720

$cm^{-1}$, of Si-O-Si bond at 1,080 $cm^{-1}$ and 1,040 $cm.^{-1}$, of $-CH_3$ group at 2,950 $cm^{-1}$, 1,400 $cm.^{-1}$ and 1,300 $cm^{-1}$, and of $-Si-(CH_3)_3$ group at 845 $cm.^{-1}$ no absorption of epoxy group at 910 $cm.^{-1}$ was observed.

The result of the elemental analysis was as follows:
Calculated for $C_{17}H_{38}O_6Si_3$: C 48.3%; H 9.0%
Found: C 49.7 %; H 9.3 %

From the above results, it was confirmed that the product was SiGMA.

Reference Example 2

Synthesis of SiGEMA
[Methyldi(trimethylsiloxy)sylylpropylglycerolethyl Methacrylate]

A one liter four neck round bottom flask equipped with a magnetic stirrer, a thermometer, a tube for introducing nitrogen gas, a dropping funnel and a reflux condenser was charged with 260 g. of ethylene glycol monomethacrylate, 7 g. of triethylamine and 4 g. of hydroquinone. With introducing nitrogen gas into the flask, 336 g. of methyldi(trimethylsiloxy)sylylpropylene oxide was added dropwise to the flask through the dropping funnel with stirring. The mixture was then gradually heated to 85° C., and at this temperature the reaction was carried out for about 6 hours. After the completion of the reaction, the reaction mixture was allowed to cool and then admixed with a large quantity of n-hexane. The mixture was washed several times with a 0.5N aqueous solution of sodium hydroxide by employing a separatory funnel until the aqueous solution became colorless, and further washed with a saline water until it was neutral. After dehydrating by Glauber's salt for a day and night, the mixture was filtered and then n-hexane was removed by an evaporator. The thus purified reaction product was a slightly viscous, yellow-tinged. transparent liquid. The yield was 60%.

According to the quantitative analysis by gas chromatography, the purity was over 93%.

Also, the refractive index $n_D^{20}$ of the product was 1.4372.

The infrared absorption spectrum of the product indicated absorptions of —OH group at 3,420 $cm.^{-1}$, of double bond at 1,640 $cm.^{-1}$, of ester bond at 1,720 $cm.^{-1}$, of Si—O—Si bond at 1,080 $cm.^{-1}$ and 1,040 $cm.^{-1}$, of '$CH_3$ group at 2,950 $cm.^{-1}$, and of $-Si-(CH_3)_3$ group at 845 $cm.^{-1}$ The result of the elemental analysis was as follows:
Calculated for $C_{19}H_{42}O_7Si_3$: C 48.9% ; H 9.0%
Found: C 47.2%; H 8.7%

From the above results, it ws confirmed that the product was SiGEMA.

EXAMPLE 1

Fifty-five grams of SiGMA, 10 g. of ethylene glycol monomethacrylate, 5 g. of ethylene glycol dimethacrylate, 30 g. of methyl methacrylate and 0.08 g. of azobisdimethylvaleronitrile were thoroughly admixed and then placed in a test tube. Under the ultraviolet irradiation, the polymerization was carried out stepwise at 15° C., for 16 hours, at 40° C. for 8 hours and then the ultraviolet irradiation was stopped and the thermal polymerization was further carried out stepwise at 60° C. for 24 hours, at 80° C. for 4 hours, at 100° C. for 4 hours and at 120° C. for 4 hours to give a colorless, transparent rod.

From the thus obtained material of contact lens in the form of rod, a piece having a diameter of 15 mm. and a thickness of 0.1 mm. was obtained by mechanical processing, and the oxygen permeability was measured. The oxygen permeability was $14.9 \times 10^{-10}$ ml.cm./$cm^2$.sec.cmHg.

The material in the form of rod was subjected to a usual mechanical processing such as cutting, grinding and polishing to give contact lenses having a base-curve of 7.90 mm., a front-curve of 8.10 mm., a center thickness of 0.13 mm. and a size of 11.5 mm. The thus prepared contact lenses were worn on rabbit eyes continuously for 21 days. No change was observed on the eyes.

The material had a refractive index $n_D^{20}$ of 1,4761 and a specific gravity of 1.11. The visible ray percent transmission of the material having a thickness of 0.15 mm. was 97.8 %. Also, the material hd good hydrophilic property. The judgement as to the hydrophilic property was conducted by immersing the contact lens in a 0.9 % by weight saline water and observing whether or not the surface of the contact lens was covered with the water when the contact lens was picked out with tweezers. When the contact lens was covered with the water, the hydrophilic property of the lens was judged as good.

EXAMPLES 2 to 7

The procedures of Example 1 were repeated except that the amounts of the monomers were changed as shown in Table 1 to give copolymers.

The properties of the obtained copolymers are shown in Table 1.

Table 1

| Example No. | Composition | | | | Appearance | Hardness | Oxygen permeability ml.cm./$cm^2$.sec.cmHg |
| | SiGMA | EGMA | EDMA | MMA | | | |
| | parts | | | | | | |
| --- | --- | --- | --- | --- | --- | --- | --- |
| 2 | 30 | 5 | 5 | 60 | T | H | $3.0 \times 10^{-10}$ |
| 3 | 40 | 7 | 5 | 48 | T | H | $6.2 \times 10^{-10}$ |
| 4 | 50 | 9 | 5 | 36 | T | H | $11.4 \times 10^{-10}$ |
| 5 | 60 | 11 | 5 | 24 | T | H | $18.4 \times 10^{-10}$ |
| 6 | 70 | 13 | 5 | 12 | T | H | $25.5 \times 10^{-10}$ |
| 7 | 80 | 10 | 5 | 5 | T | SS | $31.8 \times 10^{-10}$ |

(Note)
EGMA: Ethylene glycol monomethacrylate
EDMA: Ethylene glycol dimethacrylate
MMA: Methyl methacrylate
T: Colorless and transparent
H: Hard
SS: Semi-soft From the obtained copolymers in the form of rod, contact lenses were prepared by a usual mechanical processing. Although the rod obtained in Example 7 was somewhat hard to grind and polish, other rods were excellent in cutting, grinding and polishing. With respect to the affinity for tears, the conact lens prepared from the rod obtained in Example 7 was slightly bad, but other contact lenses were excellent.

It was possible to continuously wear for a long term the contact lenses except for those of Examples 2 and 3 under usual conditions. The contact lenses of Examples 2 and 3 could be continuously worn for a long term by using them under the conditions that the lenses had a thickness of not more than 0.1 mm. and a size of not more than 9.0 mm. and were fitted flat.

EXAMPLES 8 TO 15

Copolymers were prepared by employing 55 parts of SiGMA, 8 parts of a hydrophilic monomer, 8 parts of a cross-linking agent, 29 parts of a methacrylic acid alkyl ester monomer and 0.08 part of a free radical polymerization initiator, respectively as shown in Table 2 in the same manner as in Example 1.

The properties of the obtained copolymers are shown in Table 2.

continuously for 21 days. No change was observed on the eyes.

The material had a refractive index $n_D^{20}$ of 1.4742 and a specific gravity of 1.10. The visible ray percent transmission of the material having a thickness of 0.15 mm. was 97.3%. Also, the material had good hydrophilic property.

In comparison with SiGMA as to the effect of increasing the oxygen permeability, the effect of SiGMA was slightly larger than that of SiGEMA when the amount thereof was the same. As shown in Example 1 and this Example, the oxygen permeability of the copolymer containing SiGMA was about 1.1 times that of the copolymer containing SiGEMA.

EXAMPLE 17

Thirty grams of SiGMA, 25 g. of SiGEMA, 10 g. of ethylene glycol monomethacrylate, 5 g. of ethylene glycol dimethacrylate, 30 g. of methyl methacrylate and Table 2

| Example No. | 8 | 9 | 10 | 11 | 12 | 13 | 14 | 15 |
|---|---|---|---|---|---|---|---|---|
| Methacrylic acid ester derivative | SiGMA | SiGMA | SiGMA | SiGMA | SiGMA | SiGMA | SiGMA | SiGMA |
| Hydrophilic monomer | EGMA | T-EGMA | N-VP | EGMA | EGMA | EGMA | EGMA | EGMA |
| Cross-linking agent | EDMA | EDMA | EDMA | T-EDMA | AMA | TMTMA | EDMA | EDMA |
| Methacrylic acid alkyl ester | MMA | MMA | MMA | MMA | MMA | MMA | CHMA | MMA |
| Polymerization initiator | ABVN | ABVN | ABVN | ABVN | ABVN | ABVN | ABVN | AIBN |
| Apperance | T | T | T | T | T | T | T | T |
| Vickers hardness number | 6.3 | 4.2 | 7.4 | 5.0 | 4.6 | 9.5 | 4.9 | 8.5 |
| Oxygen peermeability ($\times 10^{-10}$ ml.cm./cm.$^2$sec.cmHg) | 14.5 | 15.0 | 14.1 | 14.8 | 15.3 | 14.7 | 15.8 | 14.3 |

(Note)
EGMA: Ethylene glycol monomethacrylate
T-EGMA: Triethylene glycol monomethacrylate
N-VP: N-vinyl pyrrolidone
EDMA: Ethylene glycol dimethacrylate
T-EDMA: Triethylene glycol dimethacrylate
AMA: Allyl methacrylate
TMTMA: Trimethylolpropane trimethacrylate
MMA: Methyl methacrylate
CHMA: Cyclohexyl methacrylate
ABVN: Azobisdimethylvaleronitrile
AIBN: Azobisisobutyronitrile
T: Colorless and transparent All copolymers obtained were colorless and transparent, and also had a sufficient rigidity and could be readily processed.

From these copolymers, contact lenses were prepared in the same manner as in Example 1 and were worn on rabbit eyes continuously for 21 days. No change was observed on the eyes.

EXAMPLE 16

Fifty-five grams of SiGEMA, 10 g. of ethylene glycol monomethacrylate, 5 g. of ethylene glycol dimethacrylate, 30 g. of methyl methacrylate and 0.08 g. of azobisdimethylvaleronitrile were thoroughly admixed and then placed in a test tube. The monomers were thermally polymerized by stepwise raising the polymerization temperature. That is to say, the thermal polymerization was carried out at 40° C. for 64 hours, at 60° C. for 24 hours, at 80° C. for 4 hours, at 100° C. for 4 hours and at 120° C. for 4 hours to give a colorless, transparent rod.

The thus obtained material for a contact lens had an oxygen permeability of $13.5 \times 10^{-10}$ ml.cm./cm.$^2$sec.cmHg.

From this material, contact lenses having a basecurve of 7.90 mm., a front-curve of 8.10 mm., a center thickness of 0.13 mm. and a size of 11.5 mm. were prepared by subjecting the material to a usual mechanical processing. The contact lenses were worn on rabbit eyes 0.08 g. of azobisisobutyronitrile were thoroughly admixed and then placed in a test tube. Under the ultraviolet irradiation, the polymerization was carried out stepwise at 18° C. for 16 hours, at 30° C. for 4 hours, at 40° C. for 4 hours and at 50° C. for 4 hours, and then the ultraviolet irradiation was stopped and the thermal polymerization was further carried out stepwise at 60° C. for 12 hours, at 80° C. for 4 hours, at 100° C. for 4 hours and at 120° C. for 4 hours to give a colorless, transparent rod.

The thus obtained material for a contact lens had an oxygen permeability of $14.2 \times 10^{-10}$ ml.cm./cm.$^2$sec.cmHg.

From this material, contact lenses having a basecurve of 7.90 mm., a front-curve of 8.10 mm., a center thickness of 0.13 mm. and a size of 11.5 mm. were prepared by subjecting the material to a usual mechanical processing. The contact lenses were worn on rabbit eyes continuously for 21 days. No change was observed on the eyes.

What we claim is:
1. A polymerization product of
   (a) 30 to 80% of at least one monomer selected from the group consisting of methyldi(trimethylsiloxy)-sylylpropylglycerol methacrylate having the following formula

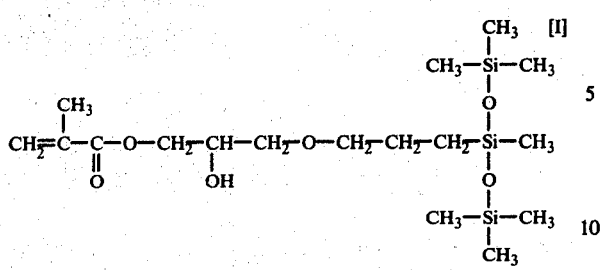

and methyldi(trimethylsiloxy)sylylpropylglycerolethyl methacrylate having the following formula

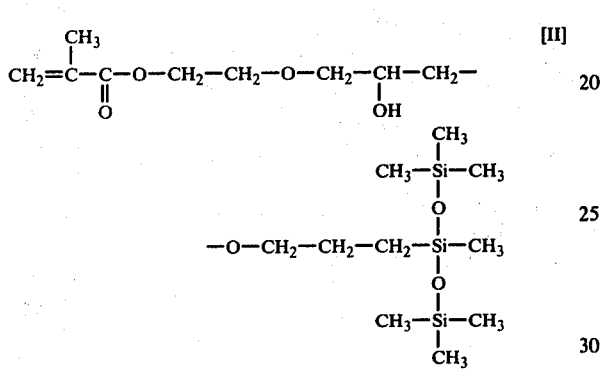

(b) 5 to 30% of at least one hydrophilic monomer selected from the group consisting of ethylene glycol monomethacrylate, diethylene glycol monomethacrylate, triethylene glycol monomethacrylate, N-vinyl pyrrolidone and dimethyl acrylamide, (c) 5 to 60% of at least one methacrylic acid alkyl ester monomer selected from the group consisting of methyl methacrylate, ethyl methacrylate and cyclohexyl methacrylate, and (d) 0.5 to 15% of at least one cross-linking agent having at least two copolymerizable functional groups selected from the group consisting of ethylene glycol dimethacrylate, diethylene glycol dimethacrylate, triethylene glycol dimethacrylate, allyl methacrylate, divinyl benzene, diallyl phthalate and trimethylolpropane trimethacrylate, said % of (a), (b), (c) and (d) being % by weight based on the total weight of (a), (b), (c) and (d).

2. The polymerization product of claim 1, having an oxygen permeability of $3.0 \times 10^{-10}$ to $32.1 \times 10^{-10}$ ml.cm./cm.$^2$sec.cmHg, a refractive index of $n_D^{20}$ = 1.40 to 1.49, a specific gravity of 1.08 to 1.21, a visible ray percent transmission of not less than 90% and a Vickers hardness number of 4.0 to 19.0.

3. A process for preparing a copolymer which comprises bulk-polymerizing (a) 30 to 80% of at least one monomer selected from the group consisting of methyldi(trimethylsiloxy)-sylylpropylglycerol methacrylate having the following formula

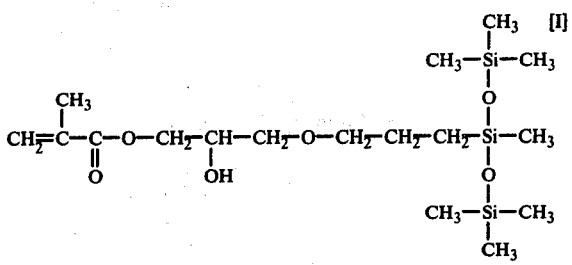

and methyldi(trimethylsiloxy)sylylpropylglycerolethyl methacrylate having the following formula

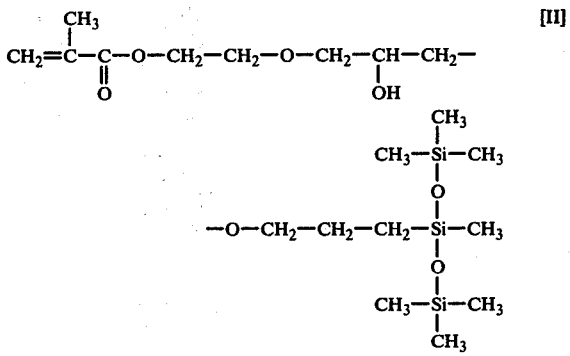

(b) 5 to 30% of a hydrophilic monomer, (c) 5 to 60% of a methacrylic acid alkyl ester monomer, and (d) 0.5 to 15% of a cross-linking agent having at least two copolymerizable functional groups, in the presence of 0.05 to 1.0 part by weight, per 100 parts by weight of the mixture of (a), (b), (c) and (d), of a free radical polymerization initiator, said % of (a), (b), (c) and (d) being % by weight based on the total weight of (a), (b), (c) and (d).

4. The process of claim 3, wherein the bulk polymerization is thermally carried out for about 60 to about 110 hours by stepwise raising the temperature from 40° to 120° C.

5. The process of claim 3, wherein the bulk polymerization is carried out first under the ultraviolet irradiation for about 30 to about 40 hours by stepwise raising the temperature from 15° to 50° C., and then thermally carried out without the ultraviolet irradiation for about 30 to 40 hours by stepwise raising the temperature from 50° to 120° C.

6. The process of claim 3, wherein said free radical polymerization initiator is at least one member selected from the group consisting of benzoyl peroxide, azobisisobutyronitrile and azobisdimethylvaleronitrile.

7. A contact lens made of a copolymer consisting essentially of (a) 30 to 80% by weight of units of at least one monomer selected from the group consisting of methyldi(triethylsiloxy)sylylpropylglycerol methacrylate having the following formula

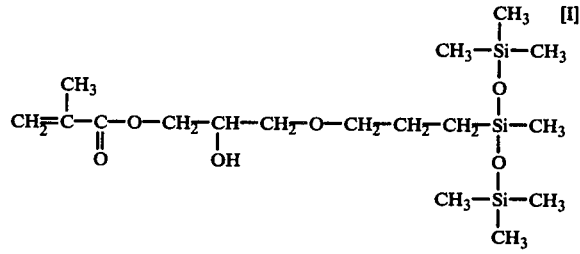

and methyldi(trimethylsiloxy)sylylpropyl-glycerolethyl methacrylate having the following formula

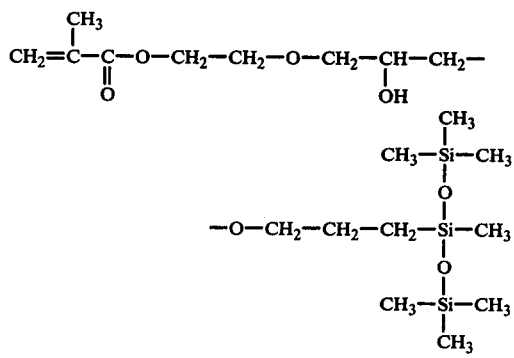

(b) 5 to 30% by weight of hydrophilic monomer units,
(c) 5 to 60% by weight of methacrylic acid alkyl ester monomer units, and
(d) 0.5 to 15% by weight of units of a cross-linking agent having at least two copolymerizable functional groups.

8. The contact lens of claim 7, wherein said hydrophilic monomer is at least one member selected from the group consisting of ethylene glycol monomethacrylate, diethylene glycol monomethacrylate, triethylene glycol monomethacrylate, N-vinyl pyrrolidone and dimethyl acrylamide.

9. The contact lens of claim 7, wherein said methacrylic acid alkyl ester monomer is at least one member selected from the group consisting of methyl methacrylate, ethyl methacrylate and cyclohexyl methacrylate.

10. The contact lens of claim 7, wherein said cross-linking agent is at least one member selected from the group consisting of ethylene glycol dimethacrylate, diethylene glycol dimethacrylate, triethylene glycol dimethacrylate, allyl methacrylate, divinyl benzene, diallyl phthalate and trimethylolpropane trimethacrylate.

11. The contact lens of claim 7, having an oxygen permeability of $3.0 \times 10^{-10}$ to $32.1 \times 10^{-10}$ ml.cm./cm.$^2$sec.cmHg, a refractive index of $n_D^{20} = 1.40$ to 1.49, a specific gravity of 1.08 to 1.21, a visible ray percent transmission of not less than 90% and a Vickers hardness number of 4.0 to 19.0.

* * * * *